United States Patent
Monroe et al.

[11] Patent Number: 5,296,026
[45] Date of Patent: Mar. 22, 1994

[54] PHOSPHATE GLASS CEMENT

[76] Inventors: Eugene A. Monroe, 13780 N. Saint Vrain Dr., Lyons, Colo. 80540; Wei-Shi Chen, P.O. Box 305, Wellsville, Ohio 43968

[21] Appl. No.: 279,448
[22] Filed: Dec. 2, 1988
[51] Int. Cl.$^5$ .............. A61C 5/00; C03C 14/00; C03C 3/16
[52] U.S. Cl. .................. 106/35; 433/228.1; 501/32; 501/45
[58] Field of Search .............. 433/228.1; 106/35; 501/32, 45

[56] References Cited

U.S. PATENT DOCUMENTS

| | | | |
|---|---|---|---|
| 2,450,952 | 10/1948 | Greger | 106/35 |
| 3,510,322 | 5/1970 | Higashi et al. | 106/35 |
| 3,873,327 | 3/1975 | Duff | 106/35 |
| 3,913,229 | 10/1975 | Driskell | 433/228 |
| 4,097,935 | 7/1978 | Jarcho | 623/16 |
| 4,123,416 | 10/1978 | Potter | 860/605 |
| 4,135,935 | 1/1979 | Pfeil et al. | 501/32 |
| 4,149,894 | 4/1979 | Ebihara et al. | 106/35 |
| 4,308,064 | 12/1981 | Takami et al. | 501/135 |
| 4,518,430 | 5/1985 | Brown | 106/35 |

FOREIGN PATENT DOCUMENTS

| | | | |
|---|---|---|---|
| 2827635 | 1/1980 | Fed. Rep. of Germany | 433/228.1 |
| 2041954 | 9/1979 | United Kingdom | 433/228.1 |

*Primary Examiner*—Paul Lieberman
*Assistant Examiner*—John Boyd

[57] ABSTRACT

Disclosed are useful and unique glass phosphate cement compositions and methods for their use as surgical implant materials to fill cavities in bone and canals in teeth. The cement compositions consist of glass powders having a range of chemicals including $P_2O_5$, CaO, SrO and $Na_2O$ in combination with an aqueous liquid and with or without therapeutic agents. Mixing the powder and liquid results in a hardening reaction. When the cement is implanted into hard tissue, it serves as a filler/graft material and along with the release of leachable constituents it can assist in the healing and maintenance of healthy bone.

8 Claims, 2 Drawing Sheets

SOLUBILITY OF THE CEMENT IN EXAMPLE 1

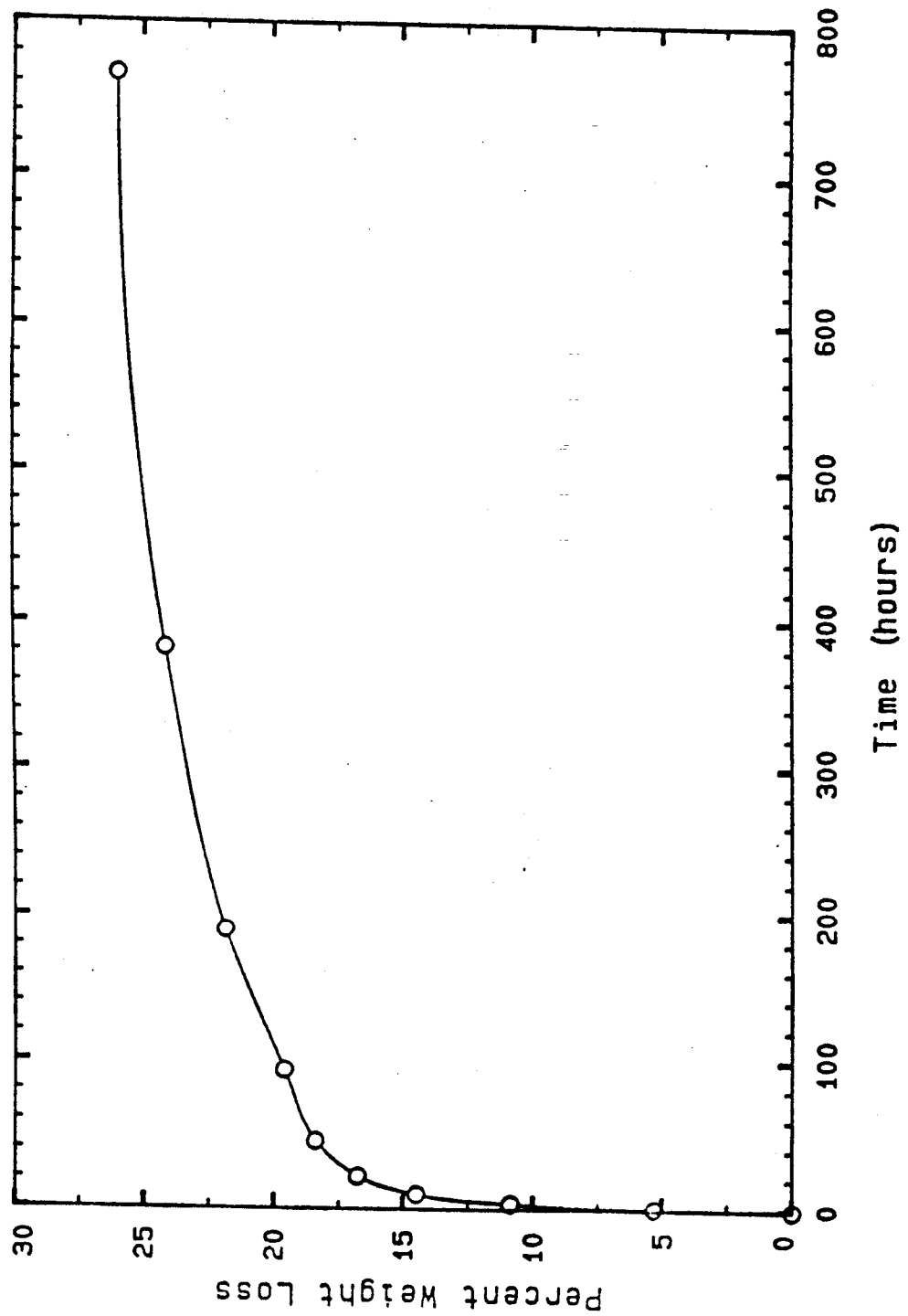
Fig.1. SOLUBILITY OF THE CEMENT IN EXAMPLE 1

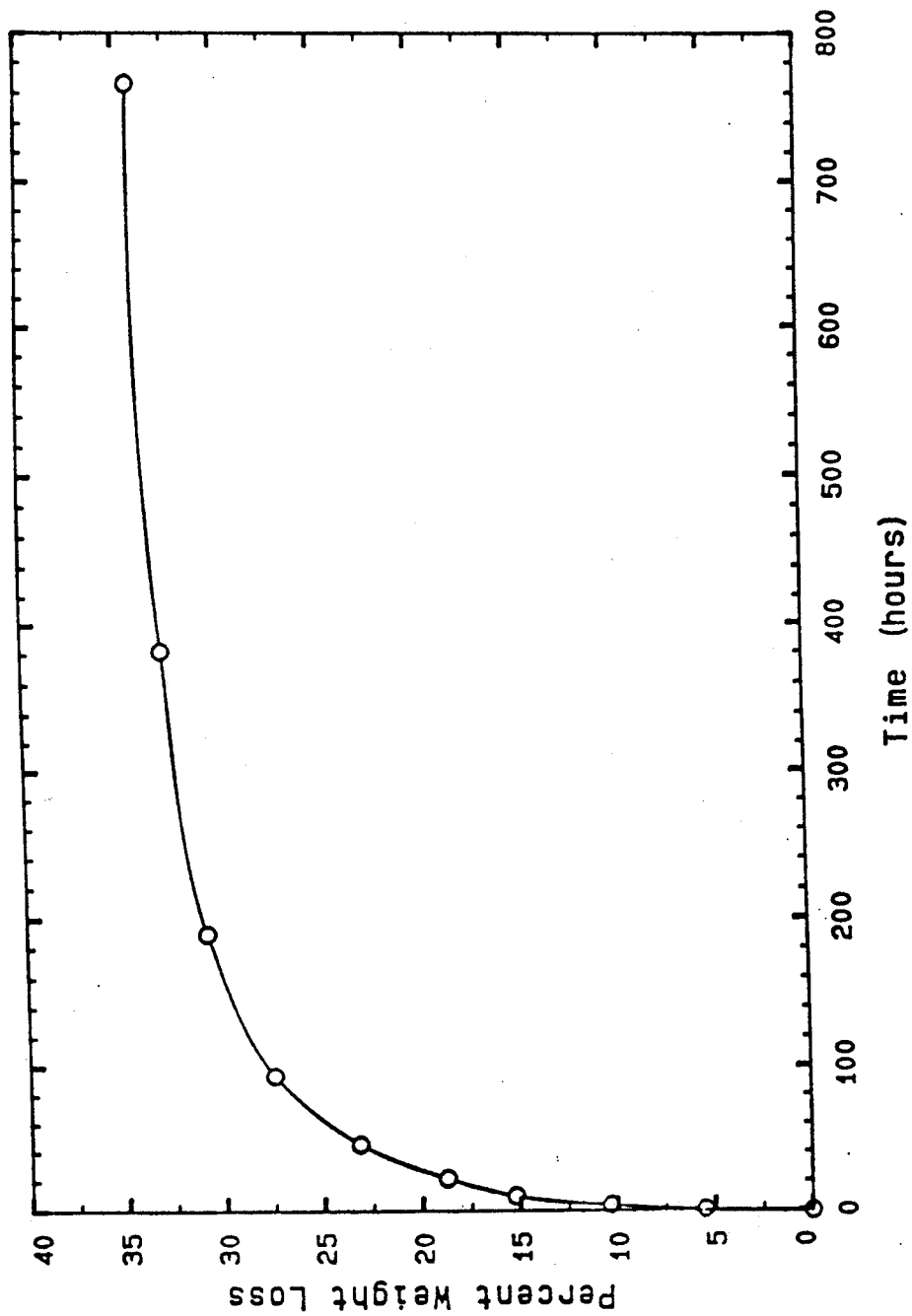
Fig. 2. SOLUBILITY OF THE CEMENT IN EXAMPLE 2

PHOSPHATE GLASS CEMENT

BACKGROUND

1. Field of Invention

This invention relates to ceramic cements and specifically to a new phosphate glass cement for hard tissue surgical implants and prostheses for man and animals in the dental, medical and veterinarian fields.

2. Description of Prior Art

In dental and medical practice, several different ceramic and glass materials are used for bone grafts and other prosthetic applications. These mainly contain calcium and phosphorus, the elements present in the mineralized tissue of bone and teeth.

Heretofore, some of these prosthetic ceramic materials set up and harden as a true cement whereas others are powder which when mixed with an aqueous media to form suspensions or pastes do not harden.

One such prosthetic material is Plaster of Paris powder, which upon mixing with water is placed in bony defects, thereupon hardening. Beginning in the 1800's and still in limited use today, this substance of $CaSO_4 \cdot 2H_2O$ is resorbed by the body but is unpredictable as to its efficacy in stimulating bone to heal normally.

A second ceramic bone graft substance is an organic bone, that is, bovine bone with the organic components removed to leave the calcium phosphate mineral powder, essentially an apatite, $Ca_5(PO_4,CO_3)_3(OH)$. It becomes a paste when mixed with water but not a cement with the disadvantage the particles can migrate and wash out from the implant site.

A third bone graft material is of synthetic calcium phosphate apatite in the U.S. Pat. No. 4,097,935 to M. Jarcho, 1978 Jul. 4. Used as a coarse powder paste without hardening, the material can migrate from the site and is not considered biodegradable although a more recent form of apatite called OsteoGen of Impladent, Inc. is regarded as resorbable.

A fourth ceramic graft in the U.S. Pat. No. 3,913,229 to T. Driskell and others, 1975 Oct. 21, is a non-apatite powder called tricalcium phosphate, $Ca_3(PO_4)_2$ used as a paste. This substance is biodegradable but is not a cement.

Prosthetic cements made of various calcium phosphate powders and an aqueous reacting liquid were recently reported. H. Morima and others in the journal *Gypsum Lime*, 188 11-16 (1984) made a cement of alpha-$Ca_3(PO_4)_2$ powder. In the patent JP 59,182,263, 1984 Oct. 17, $Ca_3(PO_4)_2$ cements that solidify with 4N $HNO_3$ were proposed for the repair of bones and teeth. W. Brown and L. Chow in U.S. Pat. No. 4,518,430, 1985 May 21, invented bone and tooth prosthetic cements from various calcium phosphate powders such as $CaHPO_4 \cdot 2H_2O$ and $Ca_8(PO_4)_2O$ mixed with acidic or basic water solutions.

In addition to the crystalline calcium phosphate and calcium sulfate bone graft ceramics listed above, there are several biologically compatible glasses containing calcium and phosphorus used as a non-cement prosthetic bone material. The best known of these is called Bioglass which is basically a silicate glass and non-resorbable with applications as coating on metals or as a solid bone prosthesis.

A more recent prosthetic glass based on a phosphate rather than silicate composition and containing CaO and other cations in the patent Appl. GB 2,178,422 to C. Drake, 1987 Feb. 11, is a dissolvable implant, but not a cement.

Besides the phosphate-containing implant glasses, none of which are cement systems, there do exist glass cements for the purpose of dental restorations, but not for surgical implants or bone grafting. The oldest of these is the so called silicate cement used for anterior tooth filling first introduced in the late 1800's of obscure origin. It is a silicate glass powder including ions of calcium, aluminum, sodium, and fluorine which when reacted with water solution of phosphoric acid hardens into a translucent cement. A more recent and dentally important modification of the silicate cement is the so called glass ionomer cement patented by A. Wilson and B. Kent, Ger 2,061,513 in 1971 June 24. This ionomer glass uses a silicate glass powder very similar to the silicate cement, but reacts the powder with an aqueous solution of polyacrylic acid or a copolymer of acrylic and itaconic acids. W. Potter and others invented a modification of the ionomer cement by using a reacting solution of polycarboxylic acid in the U.S. Pat. No. 4,123,416 of 1978 Oct. 31.

OBJECTS AND ADVANTAGES

Accordingly, several objects and advantages of the invention are: to provide a surgical or endodontic implant cement compatible with bone, to provide a cement that when mixed will yield a plastic consistency that can be manipulated in shape and easily implanted into the bone or tooth cavity wherein the substance will harden and not easily migrate or wash out from the site, to provide a cement of chemical composition similar to bone and tooth mineral, essentially of calcium, phosphorus, oxygen and water, to provide a cement that can be degraded or partially resorbed in the body, to provide a cement that can be formulated with autogenous bone graft, to provide a cement for filling periodontal, periapical, osteomyelitic, traumatic, cystic and other bone defects, to provide a cement for preservation of the alveolar ridge, sinus augmentation, and root canal filling.

In addition, we claim the additional object and advantage: to provide a surgical cement that is capable of releasing chemical substances or drugs incorporated into the cement over a period of time due to the nature of certain formulations of the cement being degradable in the body environment.

Further objects and advantages of our invention will become clear from a consideration of the ensuing description of it.

BRIEF DESCRIPTION OF THE DRAWINGS

FIG. 1 shows a plot of the degradation of the cement of Example 1 over time

FIG. 2 gives the degradation of the cement of Example 2 over time.

DESCRIPTION OF INVENTION

This phosphate glass cement invention consists of a two component system, the glass powder and the liquid reactant. Mixing these said components together results first in a putty-like paste. The paste is placed in the surgical site wherein it hardens into a biocompatible cement capable of slowly degrading to release ions of calcium and phosphorus and perhaps others conducive to bone healing and growth.

A wide range of chemical compositions can be used in making the phosphate cement. The selection of a particular composition and formulation procedures determines the properties of the cement including the paste consistency, hardening time, final pH, reaction products and composition of the matrix binder of the cement, dissolution in an aqueous environment, and the mechanical and physical properties of the cement.

The chemical composition of the glass suitable for making cements ranges from 30–60 mol % $P_2O_5$, 20–58 mol % CaO, 0–35 mol % SrO, and 0–30 mol % $Na_2O$. Other useful compounds for modifying the properties of the glass include but are not limited to the following: $NaF$ or $CaF_2$, $Al_2O_3$, $ZnO$, $MgCO_3$, $B_2O_3$, $NO_3$, $K_2O$, and $Li_2O$. The raw materials used for preparing the glass and supplying the major oxides were $NH_4H_2PO_4$ for $P_2O_5$, $Ca(OH)_2$ for CaO, $Na_2CO_3$ for $Na_2O$ and $SrCO_3$ for SrO. The raw materials were dried in an oven for 4 hours, weighed to prepare the selected glass batch, ground in a mortar, and mixed together in a rotary mixer for ½ hour. To remove the NH vapor before melting, the batch was heated at 150° C. for 1 hour, then at 300° C. for 1.5 hours, after which the batch was ground and rotary mixed as before.

The glass batches were melted in the temperature range from 1100°‑1360° C. for 40 minutes and then quenched by pouring out between steel plates, or, in the case of the composition with a tendency to devitrify, by pouring into water followed by oven drying at 120° C. for 4 hours. After melting and quenching, the glasses were ground until they passed through a 230 mesh sieve. Then the powder was further reduced in size to less than 10 $\mu$m, as determined by microscopy and a Leed & Northrup Co. Microtrac Particle Size Analyzer, by using a vibration mill for 2½ hours.

The liquid component of the cement system that reacts with the fine glass powder was either a 20–50 weight percent aqueous solution of orthophosphoric acid or water along with a measured amount of calcium hydroxide powder added to the glass powder. The choice of the acid or the basic reacting liquid was determined by the particular glass composition that was chosen. Besides these two reacting liquids other aqueous solutions that result in an acid-base reaction can be used, such as sodium phosphate. Other additives may be introduced into the liquid such as seed crystals or chemicals that act to accelerate or retard the hardening reaction.

The set-up or hardening of the cement results from the chemical reaction that occurs between the powder and liquid with the formation of a new crystalline, and/or amorphous phase which acts as a binder or cementing agent and binds any remaining unreacted glass powder. The examples that follow will further elucidate the nature of the binder agent.

The composition of these prosthetic cements were selected to be compatible with hard tissues of the body. In addition to being compatible and acting as fillers and a physical stimulus in bone defects, tooth sockets and tooth canals, these cements may have an osteoconductive or osteogenic attribute whereby they may provide a conducive chemical envirorinent for the formation of new healing bone. Many scientific reports exist in the literature which suggest calcium phosphate substances in powder or porous solid form, such as tricalcium phosphate, $Ca_3(PO_4)_2$ and hydroxyapatite stimulate or mediate the development of new bone in diseased, injured or atrophic bone sites. The apatite graft is believed to be rather inert and not appreciably resorbed whereas the tricalcium phosphate is reportedly resorbable by the body. The cement of this invention is in the latter category of being more or less resorbable depending upon the specific cement formulation. After one month the percent weight loss of disc-shaped soluble type cement samples 10 mm diameter by 1 mm thick placed in boiled distilled water of pH 6.0–6.8 ranged from about 20 to 60 depending upon the particular cement composition.

In addition to the powder and liquid cement components, various therapeutic agents may be introduced into the powder or liquid phases. In the case of post-extraction alveolitis or dry socket and osteomyelitis, the addition of an antibiotic such as one of the penicillinase—resistant penicillin, oxacillin, methicillin, or other antibiotics such as cephalosporin, erthyromycin or gentamicin may be advantageous in promoting bone healing. The antibiotic would be released as the cement graft degrades. In the case of patients suffering from periodontitis, one of the tetracycline drugs can be added to the cement grafts which is placed into the bony defect. Since tetracycline is known to chemically bond to substances containing divalent or trivalent cations including bone, this drug will bond to the cement graft material of this invention as can be demonstrated by fluorescent microscopy. Thus, the drug becomes an integral part of the graft, being slowly released as the graft degrades.

In order to prepare a cement for clinical application, the sterilized powder and liquid components are mixed together by spatulation on a sterile glass slab which may be precooled in order to prolong the setting time. The proper powder to liquid ratio must be used in order to obtain a workable paste consistency, and the powder must be wetted by the liquid by filling the pore space of the powder with only a small excess of liquid to achieve the desired consistency. A typical powder to liquid ratio in grams per milliliter ranges from 1.5 to 3.0. Upon mixing to the putty-like consistency the cement is ready to be placed into the surgical site of the bone or tooth using a variety of dental instruments for handling plastic-like materials including syringes and amalgam carriers.

The invention will be further illustrated by the following examples.

EXAMPLE 1

A phosphate glass composition of 30 $P_2O_5$, 30 Cao, 30 SrO and 10 $Na_2O$ in mol % was melted at 1320° C. for 40 minutes, quenched in water, dried, ground and milled to less than 10 size particles. This powder was reacted with 30% phosphoric acid solution using a powder to liquid ratio in grams per milliliter of about 1.8. The time for hardening at 37 C. and 100% humidity determined by the indentation test procedure of the American National Standards/American Dental Association Specification No. 9 for Dental Silicate Cement, 1980 was about 25 minutes. The binder matrix phase was brushite, $CaHPO_4.2H_2O$ and possibly also a hydrated amorphous phase. The pH of the cement was approximately 4.0 at the end of 1 hour, 5.2 at 24 hours and 5.6 at 72 hours. The diametral tensile strength using the standard procedure for silicate dental cements, Specification No. 9, American National Standards/American Dental Association, 1980, was about 2.5 N/mn$^2$ and increased to about 6.0 N/mm$^2$ when the powder to liquid ratio was increased. The degradation of the cement in water was tested by placing a disc of cement 10 mm by 1 mm on a elevated screen in a container with 40 ml of static distilled water, having a pH of about 6.4 and at 37° C. At intervals of time the weight loss was measured and the water refreshed. The cumulative weight loss after 32 days was about 26 percent. FIG. 1 gives the degradation of this cement over time.

EXAMPLE 2

This second example is of a phosphate glass cement where calcium hydroxide was used as the reactant with the glass powder. The glass composition of 50 $P_2O_5$, 20 CaO and 30 $Na_2O$ in mol % was melted at 900° C. for 40 minutes, quenched in air between metal plates, ground and milled to less than 10 μm. Added to this glass powder was about 28 wt.% powder of the reactant, $Ca(OH)_2$. The powder was reacted with distilled water using a glass powder to liquid ratio of 1.78. The water solubilized the two powder constituents resulting in a reaction and hardening in about 7 minutes with an amorphous binder developed reaction product developed which serves to bind and harden the cement. The degradation in water following the same method as given in Example 1 was about 34% weight loss in 32 days. FIG. 2 gives the degradation of this cement over time.

It should be understood that the foregoing disclosure emphasizes certain embodiments and uses of the invention and this should not be construed as limitations on the scope of the invention, but rather as an exemplification. Many other variations are possible by using various chemical combinations in the glass and liquid components of the cement. Accordingly, the scope of the invention should not be determined by embodiments given here, but by the appended claims and their legal equivalents.

We claim:

1. A cement system consisting of an aqueous liquid and a phosphate glass powder which is reacted by mixing the liquid and powder together in the ratio of 1.5 to 3.0 grams per milliliter to yield a hardened cement composed of 1) any remnant unreacted glass powder and 2) a reaction product called the cementing binder which fills voids between and adheres to any remnant glass powder.

2. The cement of claim 1 wherein the said glass powder for making the cement ranges in chemical composition from 30-60 mol % $P_2O_5$, 20-58 mol % CaO, 0-35 mol % SrO, and 0-30 mol % $Na_2O$, with or without one or more of the modifying compounds selected from the group consisting of NaF, $CaF_2$, $Al_2O_3$, ZnO, $MgCO_3$, $B_2O_3$, $NO_3$, $K_2O$, and $Li_2O$, each in amounts ranging up to 15 mol %.

3. The cement of claim 1 wherein the aqueous liquid that reacts with the glass powder is water or water plus the addition of phosphoric acid which is conducive to the formation of a surgical cement.

4. The cement of claim 1 wherein the cement can be implanted into bony cavities and defects and into tooth canals, after mixing the powder component and the liquid component together and while still in the unhardened paste state or after the hardening of the cement.

5. The cement of claim 1 wherein the powder and liquid components can be reacted together and while still in a paste consistency can be used as a grouting, filling, plastering, grafting or cementing material for medical, dental, veterinarian or non-health related applications.

6. The cement of claim 1 wherein the cement is formed into hardened pellets, granules, cakes, or other forms for use as a mineral nutrient for living organisms.

7. The cement of claim 1 wherein the hardened surgically implanted cement is soluble, leachable and degradable, providing a chemical environment conducive to bone healing and development.

8. The cement of claim 1 wherein the glass powder contains glass plus one or more enhancing agents of: 1) $Ca(OH)_2$ powder for enhancing the chemical reaction of the cement; and 2) one or more substances selected from the group consisting of autogenous bone fragments, calcium phosphate compounds, and pharmaceutical agents including antibiotics and bone growth stimulators for enhancing the efficacious behavior of the cement after surgical implantation.

* * * * *